United States Patent
Young et al.

(10) Patent No.: US 6,673,540 B1
(45) Date of Patent: Jan. 6, 2004

(54) CELL SYSTEMS HAVING SPECIFIC INTERACTION OF PEPTIDE BINDING PAIRS

(75) Inventors: Kathleen H. Young, Newtown, PA (US); Bradley A. Ozenberger, Yardley, PA (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/714,258

(22) Filed: Nov. 17, 2000

Related U.S. Application Data

(63) Continuation of application No. 09/305,483, filed on May 6, 1999, now Pat. No. 6,284,519, which is a continuation of application No. 08/259,609, filed on Jun. 14, 1994, now Pat. No. 5,989,808.

(51) Int. Cl.$^7$ ............... C12Q 1/68; C12Q 1/02; G01N 33/53

(52) U.S. Cl. ............ 435/6; 536/23.1; 536/24.1; 435/7.1; 435/7.2; 435/7.31; 435/29; 435/440; 435/243; 435/320.1

(58) Field of Search ............ 536/22.1, 23.1, 536/23.4, 24.1; 435/4, 6, 7.1, 7.2, 7.31, 8, 29, 69.1, 69.7, 69.9, 71.1, 89, 91.1, 91.4, 440, 455, 471, 476, 479, 481, 483, 320.1, 243, 252.3, 254.1, 254.11, 255.1, 255.2, 255.5, 256.1, 260, 325

(56) References Cited

U.S. PATENT DOCUMENTS

| | | | |
|---|---|---|---|
| 5,283,173 A | 2/1994 | Fields et al. | 435/6 |
| 5,512,473 A | 4/1996 | Brent et al. | 435/252.33 |
| 5,525,490 A | 6/1996 | Erickson et al. | 435/29 |
| 5,582,995 A | 12/1996 | Avruch et al. | 435/7.1 |
| 5,989,808 A | * 11/1999 | Young et al. | 435/6 |

FOREIGN PATENT DOCUMENTS

| | | |
|---|---|---|
| WO | WO 94/09133 | 4/1994 |
| WO | WO 95/18380 | 7/1995 |
| WO | WO 95/19988 | 7/1995 |
| WO | WO 95/26400 | 10/1995 |

OTHER PUBLICATIONS

Catterall, Yeasty brew yields novel calcium channel inhibitor, Nature Biotechnology, vol. 16 (10):906 (1998).
Chien et al., The Two Hybrid System: A Method to Identify and Clone Genes for Proteins That Interact With a Protein of Interest, Proceedings of the National Academy of Sciences of USA, 88:9578–82 (1991).
Dohlman et al., Annu. Rev. Biochem., 60:653–88 (1991).
Dower S., Advances in Second Messenger and Phosphorprotein Research, 28:19–25 (1993).
Durfee et al., Genes and Devel., 7:555–69 (1993).
Fields et al., The two–hybrid system: an assay for protein–protein interactions, Trend in Genetics, vol. 10(8):286–292 (1994).
Fields et al., Nature, 340:245–66 (1998).
Fritz, C., et al., Current Biology, 2:403–05 (1992).
Garbers, The guanylyl cyclase receptor family, New Biol., vol. 2(6):499–504 (1990) (Abstract).
Kim et al., "Inhibition of vascular endothelial growth factor–induced angiogenesis suppresses tumour growth in vivo," Nature, 362:841–44 (1993).
Klein et al., Recombinant Microorganisms as Tools for High Throughput Screening for Nonantibiotic Compounds, Journal of Biomolecular Screening, vol. 2(1):41–9 (1997).
Mendelsohn et al., "Applications of interaction traps/two–hybrid systems to biotechnology research", Curr. Opin. Biotech. 5:482–486 (1994).
Ozenberger et al., Investigation of Ligand/Receptor Interactions and the Formation of Tertiary Complexes, in The Yeast Two–Hybrid System, (P. Bartel and S. Fields, eds.) Oxford University Press, Inc., New York, pp. 158–172 (1997).
Phizicky et al., Protein–Protein Interactions: Methods for Detection and Analysis, Microbiological Reviews, vol. 59(1):94–123 (1995).
Vojtek et al., Mammalian Ras Interacts Directly with the Serine/Threonine Kinase Raf, Cell, 74: 205–14 (1993).
Wang et al., Science, 265:674–76 (1994).
Wu et al., "Specific interactions between proteins implicated in splice site selection and regulated alternative splicing," Cell, 74:1061–70 (1993).
Yamaguchi et al., The primary structure of the rat guanylyl cyclase A/atrial natriuretic peptide receptor gene, J. Biol. Chem., vol. 265(33):20414–20 (1990) (Abstract).
Yang et al., A Protein Kinase Substrate Identified by the Two–Hybrid System Science; 257:680–82 (1992).
Young et al., Current Biology, 3:408–20 (1992).

* cited by examiner

*Primary Examiner*—David Guzo
*Assistant Examiner*—David Lambertson
(74) *Attorney, Agent, or Firm*—Finnegan, Henderson, Farabow, Garrett & Dunner, L.L.P.

(57) ABSTRACT

This invention relates to modified host cells which express heterologous fused proteins and methods of screening for test samples having peptide binding activity; wherein the modified host cell comprises: (a) a gene sequence encoding a heterologous fusion protein; the fusion protein comprising a first peptide of a peptide binding pair, or segment of the first peptide, which is joined to either a DNA binding domain or its corresponding transcriptional activation domain of a transcriptional activation protein; (b) a gene sequence encoding a heterologous fusion protein, the fusion protein comprising a second peptide of the peptide binding pair in (a), or a segment thereof, fused to either a DNA binding domain or its corresponding transcriptional activation domain, whichever one is not employed in (a); (c) a reporter gene operatively associated with the transcriptional activation protein, or a portion thereof; (d) optionally, a deletion or mutation in the chromosomal DNA of the host cell for the transcriptional activation protein if present in the selected host cell.

60 Claims, 4 Drawing Sheets

CELL SYSTEMS HAVING SPECIFIC INTERACTION OF PEPTIDE BINDING PAIRS

This application is a continuation of application Ser. No. 09/305,483, filed May 6, 1999, now U.S. Pat. No. 6,284,519 which is a continuation of application Ser. No. 08/259,609, filed Jun. 14, 1994, issued on Nov. 23, 1999, as U.S. Pat. No. 5,989,808, each of which is incorporated by reference herein.

FIELD OF THE INVENTION

This invention relates to novel cells which express heterologous fused proteins and methods of screening for compounds having peptide-binding activity; wherein the methods employ the novel cells of this invention.

BACKGROUND OF THE INVENTION

The specific binding of a pair of peptides to each other triggers a vast number of functions in a living cell. For example, the specific binding of a ligand to a surface receptor serves as the trigger for cellular responses to many external signals. In mammals, cells respond to a wide variety of circulating peptide hormones, often through single transmembrane domain receptors. It is certainly recognized that the cytokine receptor superfamily illustrates the diverse aspects of cellular function, and physiological responses. Recent examinations of cytokine receptor function have revealed differing ligand-receptor protein stoichiometries including both 2-protein (ligand/receptor) (Cunningham et al., 1991; Staten et al., 1993) and 3-protein (ligand/receptor/receptor or ligand/receptor/transducer) interactions (Young, 1992; Taga and Kishimoto, 1992; Mui and Miyajima, 1994). The intricacies of such protein associations have been investigated using in vitro, often laborious, methods (Fuh et al., 1992; 1993; Davis et al., 1993) since genetically malleable expression systems have been unavailable. The present invention is directed to novel modified host systems which can be used for such protein investigations, yet the novel systems are significantly less laborious.

Recently reported systems in the art refer to a "2-hybrid" system as discussed by Fields and Song, 1989 and also Chien et al., 1991. The "2-hybrid" system involves differential interactions between the separable DNA binding and activation domains of the yeast transcriptional activator, Gal4. Heterologous proteins are expressed as hybrid proteins fused to either half of Gal4 (See FIG. 1; Fields and Song, 1989; Chien et al., 1991 for discussion of the 2-hybrid system). The productive interaction of the heterologous proteins brings the two halves of the Gal4 protein in close proximity, activating expression of a scorable reporter gene. To this date, such 2-hybrid systems have been disclosed as useful for determining whether a first given test peptide sequence has binding activity for the known sequence of a second peptide; wherein the affinity of the test peptide for the known peptide is unknown. Studies using such a system have been directed to analyzing intracellular proteins such as transcription factors and kinase-target protein interactions (Yang et al., 1992; Durfee et al., 1993; Li et al., 1994).

The novel modified cells of this invention and novel methods incorporating these cells provide significant advancements for the study and discovery of peptide mimics, including ligand mimics and receptor mimics. At this time no one has developed an efficient and specific screening system to investigate these areas. By employing in the cell a peptide binding pair for which the binding affinity is known, the present invention permits the investigation of peptide binding pairs, such as a ligand and receptor, wherein the peptides bind via extracellular interactions. The present invention creates exponential advantages for the discovery of compounds which can interact as ligands for specific receptors or transducers. Potential ligands include, but are not limited to, mammalian hormones with the receptors being a cognate extracellular ligand-binding peptide. Furthermore, the present invention describes the use of cell systems which express multiple heterologous proteins, including the two heterologous fused proteins to establish the specific and reversible binding of the ligand and receptor. The specific interaction of the above-described binding is readily detected by a measurable change in cellular phenotype, e.g. growth on selective medium.

SUMMARY OF THE INVENTION

One aspect of the present invention relates to novel modified host cells for the expression of heterologous fusion proteins. The novel modified host cells comprise:

a) a gene sequence encoding a heterologous fusion protein; said fusion protein comprising a first peptide of a peptide binding pair, or segment of said first peptide, which is joined to either a DNA binding domain or its corresponding transcriptional activation domain of a transcriptional activation protein;

b) a gene sequence encoding a heterologous fusion protein, said fusion protein comprising a second peptide of the peptide binding pair in (a), or a segment of said second peptide, fused to either a DNA binding domain or its corresponding transcriptional activation domain, whichever one is not employed in (a);

c) a reporter gene operatively associated with the transcriptional activation protein, or a portion thereof.

d) optionally, a deletion or mutation in the chromosomal DNA of the yeast host cell for the transcriptional activation protein if present in the host cell.

These novel modified host cells of the present invention can be used to determine the interaction of a test sample with a selected peptide of a peptide binding pair; e.g. the cell can be used to determine the interaction of a test sample with selected ligand or receptor.

A second aspect of the present invention relates to novel modified cells and screening methods which indicate the interaction of a test sample with a selected peptide and receptor by a recognizable change in phenotype. The cell exhibits the change in phenotype only in the presence of test compound having binding affinity for a peptide of the peptide binding pair, e.g. binding affinity for a ligand or its receptor.

A third aspect of the present invention relates to novel cells and screening methods which permit determining to which peptide of a peptide binding pair a test sample binds.

A fourth aspect of the present invention relates to novel cells which express three or more heterologous components for the study of higher order multi-protein associations between three or more peptides (e.g. such as the study of ligand dependent dimerization).

Defined Terms:

The term peptide binding pair refers to any pair of peptides having a known binding affinity for which the DNA sequence is known or can be deduced. The peptides of the peptide binding pair must exhibit preferential binding for each other over any other components of the modified cell.

The term peptide as used in the above summary and herein means any peptide, polypeptide or protein, unless stated otherwise. As noted above, the peptides of a peptide binding pair can be a ligand and its corresponding receptor, or a ligand and any peptide having a known binding affinity for the ligand.

Heterologous as used in the above summary and herein means peptides which (1) are not expressed by the naturally-occurring host cell or (2) are expressed by the modified host cell by an expression method other than the expression method by which the host cell would normally express the peptide.

Unless specified otherwise, the term receptor as used herein encompasses the terms receptor, soluble receptor, transducer and binding protein. In a preferred embodiments of the invention, the receptor employed is a receptor, or soluble receptor, with receptor being more preferred.

Receptor, as used herein means plasma membrane proteins that bind specific molecules, such as growth factors, hormones or neurotransmitters, and then transmits a signal to the cells' interior that causes a cell to respond in a specific manner. This includes single transmembrane proteins.

Soluble receptor means a non-transmembrane form of a receptor which is able to bind ligand. These are receptors released from a cell either by proteolysis or by alternatively spliced mRNA.

Binding protein means proteins that demonstrate binding affinity for a specific ligand. Binding proteins may be produced from separate and distinct genes. For a given ligand, the binding proteins that are produced from specific genes are distinct from the ligand binding domain of the receptor, or its soluble receptor.

Transducer means a molecule that allows the conversion of one kind of signal into another, and the molecule is readily known as a transducer for one or more the peptides of a peptide binding pair, e.g. a transducer for a ligand/receptor group.

DETAILED DESCRIPTION OF THE INVENTION

Figure 1:
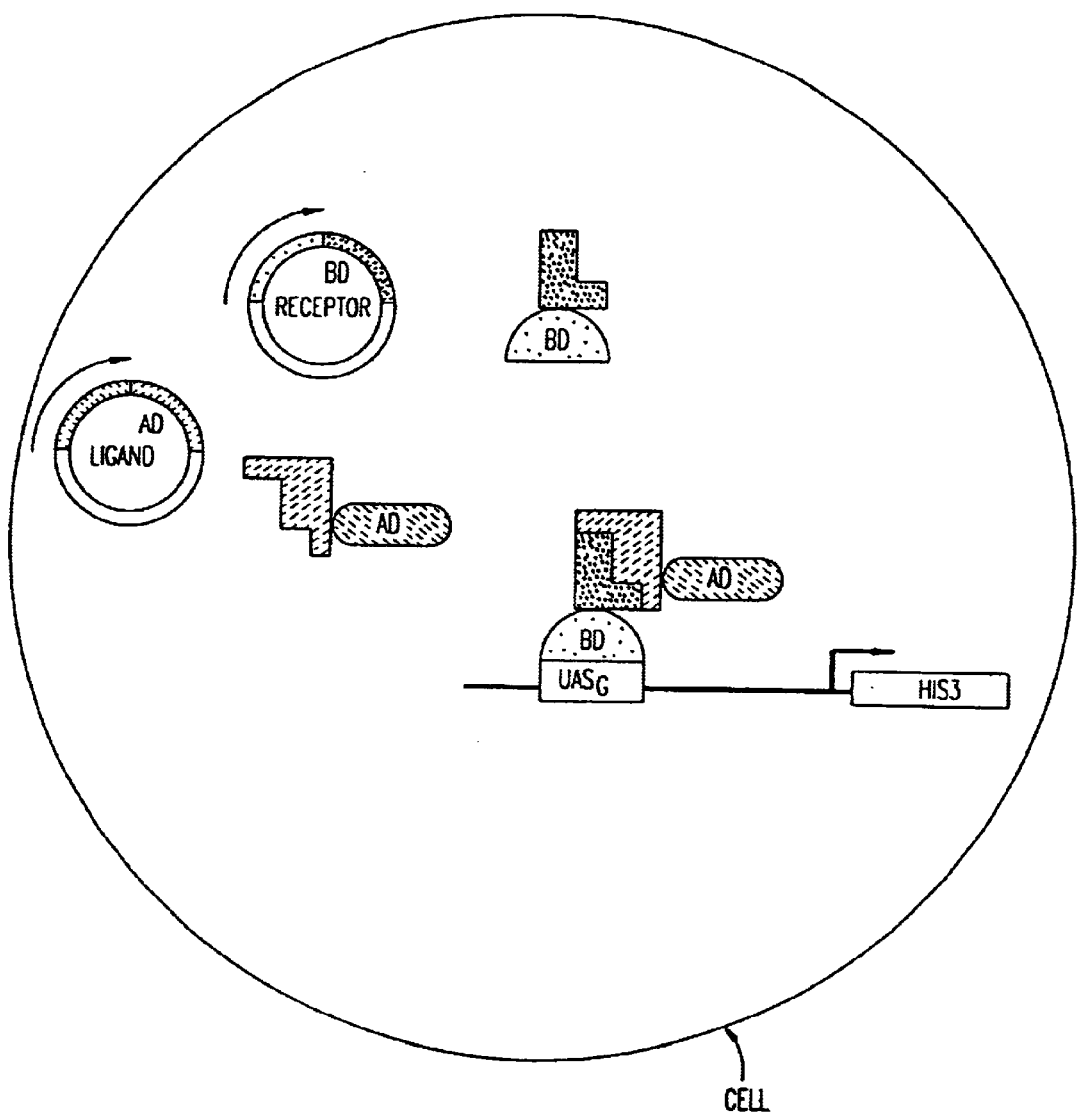
FIG. 1 is a schematic diagram of a cell which expresses from separate plasmids two heterologous fused proteins (one being the ligand fused to the activation domain of a transcriptional activation protein and the other fused protein being a receptor fused to the DNA binding domain of the transcriptional activation protein). The Figure shows the expression of the two fused proteins and the binding of the ligand and receptor, which brings together the binding domain and activation domain, reconstituting the transcriptional activation protein. Once the transcriptional activation protein is reconstituted and anchored by the DNA binding domain to the Upstream Activation Sequences (UAS) site, transcription of the reporter gene (HIS3) is initiated.

The modified cell of this invention employs a host cell. An effective host cell for use in the present invention simply requires that it is defined genetically in order to engineer the appropriate expression of heterologous fused proteins, reporter(s) and any other desired genetic manipulations. The host cell can be any eukaryotic cell, vertebrate or non-vertebrate. The host cell can be mammalian as well as amphibian, e.g. a Xenopus egg cell. Preferably, the host cell is a fungal cell, e.g. Aspergillus or Neurospora. In more preferred embodiments the host cell is a yeast cell. In alternatively preferred embodiments the yeast host cell is *Saccharomyces cerivisiae, Schizosaccharomyces pombe* or *Pichia pastoris.*

The modified host cell employs at least two genes for expressing separately the two heterologous fusion proteins. One of these fusion proteins comprises a first peptide of a peptide binding pair, or segment of said first peptide, which is joined to either a DNA binding domain, or its corresponding transcriptional activation domain, of a transcriptional activation protein. A second fusion protein comprising the second peptide of the peptide binding pair, or a segment thereof. The second peptide is fused to either a DNA binding domain or its corresponding transcriptional activation domain, whichever one is not employed in the first heterologous fused protein. The activity of the binding between the peptides of the peptide binding pairs is monitored by the use of a reporter gene, which is operatively associated with the transcriptional activation protein employed in the two fusion proteins.

The transcriptional activation protein can vary widely as long as the DNA binding domains and the activation domains are known or can be deduced by available scientific methods. The transcriptional activation protein can be any protein having two components, a DNA binding component and an activation component, wherein the transcriptional activation protein contains an acidic alpha helix for the activation of transcription. Preferably, the transcriptional activation protein is selected from Gal4, Gen4, Hap1, Adr1, Swi5, Ste12, Mcm1, Yap1, Ace1, Ppr1, Arg81, Lac9, Qa1F, VP16, LexA, non-mammalian nuclear receptors (e.g. ecdysone) or mammalian nuclear receptors (e.g. estrogen, androgens, glucocorticoids, minearalocorticoids, retinoic acid and progesterone; see also Picard et al., 1990). Preferably, the transcriptional activation protein is a yeast protein, and more preferably, the transcriptional yeast protein is selected from Gal4, Gcn4 or Adr1. It is noted that any DNA binding protein can be used which functions with an activation domain. A DNA binding protein can be substituted for the DNA binding domain of a transcriptional activation protein if the recognition sequences operatively associated with the reporter gene are correspondingly engineered. Illustrative of non-yeast DNA binding proteins are mammalian steroid receptors and bacterial LexA (see Wilson et al., 1990)

The reporter gene is generally selected in order that the binding of the domains of the transcriptional activation protein can be monitored by well-known and straightforward techniques. Preferably, the reporter gene is selected based on its cost, ease of measuring its activity and low background (i.e. the activity can be determined at relatively low levels of expression of the reporter gene because of a high signal to background ratio and/or a relatively low or no un-induced activity). The reporter can be any reporter for which its activity can be detected by any means available. Illustrative of reporters which can be used in the present invention are reporter genes selected from the group of:

a) lacZ, Luciferase gene, green fluorescent protein gene, CAT chloramphenicol acetyltransferase b) genes complementing auxotrophies, such as HIS, URA, LEU, ARG, MET, ADE, LYS, TRP.

c) gene conferring antibiotic resistance, such as $neo^r$, KAN, d) genes conferring sensitivity to a chemical such as CYH2 (cycloheximide sensitivity, CAN1 (canovanine sensitivity). In many embodiments it may be convenient for the reporter gene to prevent growth (CYH2). Preferably, the activity of the reporter gene is indicated by colorimetric or fluorescent methods and/or by measuring growth of the yeast cell.

As noted previously, the peptide employed in the modified cell is a peptide of a peptide binding pair for which the DNA sequence is known as well as the sequence of the second peptide of the binding pair. The peptides can also be peptides of a peptide binding complex which contains two or more peptides which bind each other to form the binding complex. The peptides of the peptide binding pair can be a specific ligand and a corresponding receptor or any other peptides which bind to each other preferentially, such subunits of an enzyme.

One of the significant advantages of this invention is the discovery that the modified cell employing the DNA binding and activation domains of a transcriptional protein can be used to monitor the binding of peptides of a peptide binding pair which bind through extracellular interaction. Certainly, if desired peptides which bind through intracellular interactions can also be employed in any of the novel modified cells and methods of this intention. The peptide can be from a mammalian cell or non-mammalian cell. One of the most important embodiments of the present invention relates to the application of the novel modified cells and corresponding screening methods of this invention for studying numerous mammalian peptide interactions. The mammalian peptides include mammalian ligand/receptor interactions, such as hormone/receptor interactions. Illustrative of peptide hormones which can be used in the present invention are peptides selected from, but not limited to, one of the following groups: (a) the group consisting of cytokines, interleukines, hematopoietic growth factors, insulin, insulin-like growth factors, growth hormone, prolactin, interferons, and growth factors; (b) ligands for G-protein coupled receptors; (c) ligands for nonvertebrate receptors; (d) ligands for guanylyl cyclase receptors; and (e) ligands for tyrosine phosphatase receptors.

In alternative embodiments, the peptide is a growth factor selected from epidermal GF, nerve GF, leukemia inhibitory factor, fibroblast GF, platelet-derived GF, vascular endothelial GF, tumor necrosis factor, oncostatin M, ciliary neurotrophic factor, erythropoietin, steel factor, placental lactogen and transforming GFβ.

In various preferred embodiments the peptide hormone is a ligand for a G-protein coupled receptor, such as growth hormone releasing factor, secretin, vasoactive inhibitory peptide, glucagon, thyrotropin, interleukin-8, luteinizing hormone (LH) and follicle stimulating hormone (FSH).

In additional alternative embodiments the peptide employed is a nonvertebrate peptide, such as those selected from the group consisting of plant systemin and insect differentiation peptides. However, in preferred embodiments the peptide is selected from the group consisting of mammalian peptides, and more preferably, mammalian peptide hormones.

It is also noted that specific types of receptors may also be a peptide of a peptide binding pair or peptide binding complex. Illustrative of various receptors are those selected from one of the following groups: (a) a cell adhesion molecule; (b) an immunomodulatory, antigen recognition or presentation molecule or other related peptides. Illustrative of cell adhesion molecules are ICAM, VCAM, ECAM, fibronectin, integrin, selectin and fibrinogen. Illustrative of an immunomodulatory, antigen recognition or presentation molecule are T cell receptor complex, B cell receptor complex, Fc receptors, major histocompatibility complex I, major histocompatibility complex II, CD4, CD8, CD27, CD30, MAC complex.

It is also noted that specific types of transducers may also be used as a peptide of a peptide binding pair or peptide binding complex. The transducer proteins employed can be any transducer protein which binds at least one of the peptides of the peptide binding pair or peptide binding complex. Transducer proteins include gp130, kh97, AIC2A, AIC2B.

Preferably, the heterologous fused proteins are expressed by transformation of the yeast cell with an autonomously-replicating plasmid capable of expressing the fusion protein although they can be expressed by chromosomal modification.

As noted, the screening methods of this invention are designed in order to detect the ability of a test sample to affect the binding of a peptide binding pair, e.g. ligand-receptor interaction. Basically, the method comprises determining the activity of the reporter gene upon adding a test sample to a modified host cell of the present invention under conditions suitable to detect the activity in the presence of a sample or under a condition for which the modified host cell exhibits such activity only in the presence of a sample having binding interaction with the peptide binding pair. Preferably, the activity of the reporter gene is determined by measuring a change in selected phenotype which is directly correlated to activity of the reporter.

The novel modified cells of this invention are readily applied in various screening methods for determining the binding ability of a test sample. The test sample may be a peptide, which is preferably about two amino acids in length, or a non-peptide chemical compound. The non-peptide test sample includes compounds, complexes and salts as well as natural product samples, such as plant extracts and materials obtained from fermentation broths. The modified host cells are cultured under suitable conditions for growth to study the interaction of a test sample on the binding interaction of the peptide binding pair. The modified host cells are placed in a growth medium, which preferably contains agar, with the test sample applied to the surface of the growth medium. The growth medium is preferably a conventional liquid medium of growth reagents and water, such as yeast synthetic medium (YSM available from BIO101 (also see Rose et al., *Methods in Yeast Genetics*, 1990).

One of the embodiments of the present invention is directed to a novel modified host cell and screening method which indicate the interaction of a test compound with a selected peptide binding pair by a recognizable change in phenotype. This modified host cell exhibits the change in phenotype only in the presence of test compound having binding affinity for one of the peptides of the peptide binding pair. This host cell is referred to herein as a "rescue" system. Normally, a cell response is exhibited when the two domains of the transcriptional activation protein interact. However, in a rescue system a positive indication of change in the phenotype does not occur when the two domains of the transcriptional activation protein interact. A positive indication of change in the phenotype occurs only when a test sample interrupts the interaction of the two domains of the transcriptional activation protein. In a rescue system, a modified host cell is capable of expressing at least two heterologous fusion proteins. Further, the host cell comprises: a reporter gene operatively associated with the transcriptional activation protein; wherein said reporter gene prevents the exhibition of a specific phenotype on a selective medium due to the expression of the transcriptional activation protein, or a portion thereof. A mutation in the chromosomal DNA of the host cell allows for reversal of the detectable phenotype, on the selective medium, in the absence of expression of the reporter gene. If needed, there is a deletion or mutation in the chromosomal DNA of the host cell for a transcriptional activation protein in order that transcriptional activation only occurs upon productive interaction of the selected binding pair. Only when a test sample interrupts the interaction of the two-domains of the transcriptional activation protein will the modified cell grow or survive, or exhibit another selected phenotype. Preferably, the phenotype corresponds to the growth of the cell.

Once a screening method, as discussed above, is used to determine whether a test sample interacts with, or rather disrupts, the peptide binding observed in the absence of a test sample, a secondary screen is employed to determine the specific binding affinity of the test sample, i.e. to which peptide of the peptide binding pair the test sample binds. The secondary screens employ the novel cells of this invention wherein cells are adapted to exhibit a phenotype, or phenotypic change only in the presence of a test sample which binds one peptide of the peptide binding pair. One of the preferred methods for determining the specific binding characteristics of the test sample involves employing cells which contain an effective (relatively high) copy number of either fusion protein containing one of the peptides. An effective copy number is any copy number sufficient to enable determination of the specific binding of the test sample. Preferably, the gene copy number is at least about 5, and preferably ranges from about 5 to about 50, with the higher copy numbers being the most preferred. The other fusion protein is maintained at a relatively low (1 to about 2 copies per cell) by either integration into a cell chromosome or by utilizing chromosomal centromeric sequences on the expression plasmid. If a high copy number of a first peptide is used in a cell of this invention, the cell will be more sensitive to the presence of the test sample which binds the second peptide of the peptide binding pair since the limiting amount of second peptide determines the level of the activity of the reporter gene (i.e. the change in phenotype observed). Conversely, if a high copy number of a gene encoding the second peptide of a peptide binding pair is used, the cell will be more sensitive to the presence of a test sample which binds the first peptide since the limiting amount of the second peptide determines the level of the activity of the reporter gene (i.e. the change in phenotype observed). A direct comparison of effects of a test compound on the phenotypes of the two strains (receptor>>>ligand versus ligand>>>receptor) demonstrates the specific protein interaction of the compound. As discussed supra, the genes expressing the peptides as well as the reporter gene are preferably expressed by transformation of the yeast cell with an autonomously-replicating plasmid.

An additional modified host cell of this invention is directed to cells which can be used to study peptides ligands which employ dual receptors or a receptor and a transducer for activation or transmission of a signal from the binding of multiple peptide binding components, i.e. three or more peptide binding components.

Receptor dimerization is a critical first step for signal transduction for certain classes of receptors. Dimer receptor structures can be composed of identical receptor units (examples: insulin receptor, IGF-I receptor, PDGF receptor, kinase inert domain receptor (KDR), or colony stimulating factor (CSF)-I receptor) or non-identical receptor units (example: IL-6R+gp130; insulin-IGF-I hybrid receptor; LIF+gp130; CNTF+gp130; various interferon receptors).

The components of a modified host cell for monitoring the binding activity of a peptide having "dual receptor" system are as follows: the gene sequence (a) is a gene sequence encoding a heterologous fusion protein; said fusion protein comprising one peptide of a multiple peptide binding complex, or segment of said peptide, which is joined to either a DNA binding domain or its corresponding transcriptional activation domain of a transcriptional activation protein; and the gene sequence (b) is a gene sequence encoding a heterologous fusion protein; said fusion protein comprising a second peptide of said multiple peptide binding complex, or a segment of said receptor, fused to either a DNA binding domain or its corresponding transcriptional activation domain, whichever one is not employed in (a). The modified host cell for studying a multiple peptide binding complex, such as a dual receptor system, also comprises an appropriate reporter gene and chromosomal mutations for specific analysis of the peptide (ligand/receptor) interaction as discussed infra. One can express a third peptide (e.g. a ligand) to establish a control for comparative or competitive testing.

As noted above, for the study of multiple binding peptide complexes, i.e. higher-order proteins which contain three or more peptides, one can actually use the modified host cell of the present invention to express three or more peptides. In the case of a tripeptide binding complex, any two of the peptides can be fused to the two components of the transcriptional activation protein. For example, to study the interaction of a ligand which interacts via receptor dimerization, one can express the receptors as fused proteins with the ligand being expressed as a nonfusion protein. This host cell system can be also be applied in studying multi-protein enzyme complexes. For any multiple peptide binding complex, one can identify novel peptides which interact with the complex by expressing novel proteins from random complementary DNA sequences (e.g. a cDNA library) fused to one of the domains of a transcriptional activation protein. In such a system, one of the known peptides of the peptide binding complex is fused to the other domain of the transcriptional activation protein while other units of the peptide binding complex are expressed as nonfusion peptides. It is further noted that the number of peptides expressed by the modified host cell should only be limited by the available detection means and the capacity of the host cell.

The novel screening methods can be utilized to identify compounds interacting with any peptide binding pair, e.g.

any receptor and/or ligand. Also, this modified cell system with a reporter gene to create a screen can be applied to any protein-protein interaction to discover novel compounds that disrupt that interaction. As specific examples: a) protein kinases implicated in cancers can be inserted into the system to rapidly screen for novel compounds that block the kinase-target interaction and thus may serve as unique cancer therapeutics; b) viral coat proteins, such as human immunodeficiency virus glycoproteins, and corresponding cell surface receptor proteins, such as CD4, can be inserted into the system to rapidly screen for compounds that disrupt this interaction, and may serve as anti-viral agents; c) the two subunits for the Plasmodium ribonucleotide reductase enzyme can be expressed in the system to screen for compounds which prevent this specific protein association and thus may serve as novel anti-malarial agents.

The following examples are provided to further illustrate various aspects of the present invention. They are not to be construed as limiting the invention.

EXAMPLE 1

Specific and Reversible Ligand—Receptor Interaction

Genes encoding fusion proteins are generated by cloning growth hormone (GH) and growth hormone receptor (GHR) cDNA sequences into plasmids containing the coding region for the domains Gal4. DNA binding domain (Gal4) fusions are constructed in pAS2, which is described in Wade Harper et al. Gene activation domain (Gal4) fusions are constructed in pACT-II, which is identical to pACT (described in Durfee et al., 1993) except with a modification of the polylinker region. Into the Bgl II site is added the following sequence: Bgl II-Hemagglutinin epitope-NdeI-NcoI-SmaI-BamHI-EcoRI-XhoI-Bgl II, as adapted from the polylinker sequence of pAS2 (Wade Harper et al., 1993). The cDNA encoding the mature peptide for porcine GH is generated using standard polymerase chain reaction (PCR) techniques (see Finney, 1993).

Oligonucleotides prepared on an ABI oligosynthesizer are designed according to the published cDNA sequence for pig GH (see Su and El-Gewely, 1998). A 30 base 5' oligonucleotide contains a NcoI site (5'-CATGCCATGGAGGCCTTCCCAGCCATGCCC 3' SEQ ID NO: 1) and a 27 base 3' oligonucleotide contains a BamHI site (5'-CGGGATCCGCAACTAGAAGGCACAGCT-3' SEQ ID NO: 2). The GH cDNA is generated using a pig pituitary lambda gt11 library as template source. A 540 bp fragment is obtained, ligated into pCR II vector (Invitrogen Corp.), recombinants are confirmed by restriction enzyme digest, and the DNA produced as described in Maniatus et al., 1982. The cDNA sequence is confirmed by dye-deoxy terminator reaction using reagents and protocols from Perkin-Elmer Cetus Corp. and an ABI 373A automated sequencers. The GH cDNA is directionally cloned into pACT-II via NcoI and BamHI sites. The cDNA encoding the extracellular domain of the GHR is generated using standard PCR methods. A 33 base-5' oligonucleotide containing a NcoI site (5'-CATGCCATGGAGATGTTTCCTGGAAGTGGGGCT-3' SEQ ID NO: 3) and a 39 base 3' oligonucleotide containing a termination codon, followed by a NcoI site (5'-CATGCCATGGCCTACCGGAAATCTTCTTCACATGCT GCC-3' SEQ ID NO: 4) are used to generate a 742 bp fragment encoding amino acids 1–247 of the rat GHR (Baumbach et al., 1989). This GHR cDNA is cloned into pCRII vector as previously described above, and then sub- cloned into the NcoI site of the pAS2 vector. DNA of the final recombinant vectors is transformed into yeast strain(s) by the lithium acetate method (Rose et al., 1980).

Figure 2B:
FIG. 2 contains photographs of plates which show the results of the growth experiments conducted in example 1 for the stains CY722, CY723, CY724, and CY781 on non-selective medium and selective medium, photographs A and B, respectively.
Figure 2A:

A yeast host (Y190) containing a $UAS_{GAL}$-HIS reporter gene is prepared according to the procedure described in Wade Harper et al., 1993. The genotype of strain Y190 is MATa leu2-3, 112 ura3-52 trp1-901 his3d200 ade2-101 gal4 gal80 URA3::GAL-lacZ LYS2::GAL-HIS3 cyh$^r$. Strain Y190 is transformed with both fusion constructs or with a single fusion construct plus the opposing vector containing no heterologous sequences. All strains are found to exhibit equal growth on nonselective medium (FIG. 2A). These strains are then tested for growth on selective medium (i.e. a growth medium lacking an amino acid which is synthesized by activation of the reporter gene). Only the strain containing both hybrid proteins (CY722) is able to grow while the strains containing either the ligand or receptor fusion alone do not grow (CY724 and CY723, respectively; FIG. 2B). Two independent samples of each strain are streaked on synthetic medium containing 2% glucose, yeast nitrogen base, ammonium sulfate, 0.1 mM adenine and 60 mM 3-amino-triazole (plate B) or on the same medium supplemented with histidine (plate A). Plate A is incubated at 30 C for three days; plate B for five days. These results demonstrate that GH and GHR can mediate the Gal4-dependent activation of the reporter gene in an interaction suggestive of ligand-receptor binding.

EXAMPLE 1A

Competing Expressed Free Ligand (GH) in the Presence of GH and GHR Fusion Proteins To substantiate the apparent binding of GH to its receptor in the foreign environment of a yeast nucleus, the system is modified to add a third plasmid mediating expression of "free" ligand to show that the GH peptide competes with the GH-Gal4 fusion protein, reversing the 1-hybrid interaction shown in Example 1. The parental strain Y190 (Wade Harper et al., 1993) is grown on a medium containing 5-fluoro-orotic acid to select for derivatives that spontaneously lose the URA3 gene (see Rose et al., 1990). The resultant strain, designated CY770, is utilized for all experiments examining effects of protein expressed concurrently from the third component (i.e. third plasmid). The cDNA encoding GH is generated by PCR methods using a 38 base 5' oligonucleotide containing an EcoRI site (5'-CCGAATTCAAAATGGCCTTCCCAGCCATGCCCTTGT CC-3' SEQ ID NO: 5) and a 26 base 3' oligonucleotide containing a HindIII site (5' CCAAGCTTCAACTAGAAGGCACAGCT-3' SEQ ID NO: 6) for subsequent subcloning into the vector pCUP. pCUP is an inducible yeast expression vector derived from pRS316 (Hill et al., 1996). Briefly, this vector is constructed by inserting the 3' end of the yeast PGK gene (from pPGK; Kang et al., 1990) into the pRS316 cloning region as a BamHI-SalI fragment to serve as a transcriptional terminator. To this plasmid, the CUP1 promoter region (Butt et al., 1984) is amplified by PCR as a SacI-EcoRI fragment and inserted into corresponding sites of the plasmid to create pCUP. The GH expression plasmid (GH-pCUP) is then co-transformed with the GH and GHR fusion constructs into strain CY770 to generate CY781. Concurrent expression of free GH with the GH and GHR fusion proteins (CY781) is shown to block GH-GHR-dependent cell growth on selective medium (FIG. 2B). This experiment typifies an in vivo competition assay and demonstrates the reversibility of the observed ligand-receptor interaction.

EXAMPLE 1B

Binding of Peptide Hormone Prolactin (PRL) and its Receptor

To expand and validate this technology, a similar system was developed using the peptide hormone prolactin (PRL) and its receptor. Prolactin is structurally related to GH and the prolactin receptor (PRLR) is also a member of the cytokine receptor superfamily. Unlike human GH, sub-primate GH does not readily bind the PRLR (Young and Bazer, 1989); nor does PRL readily bind the GHR (Leung et al., 1987). Mature porcine PRL is generated as a fusion to the GAL4 activation domain. Oligonucleotides are designed to pig PRL (obtained from Genbank X14068), and used to generate the mature pig PRL protein hormone from a pig pituitary lambda gt11 library using standard PCR methods. A 31 base 5' oligonucleotide includes an EcoRI site (5'-CGGAATTCTGCCCATCTGCCCCAGCGGGCCT-3' SEQ ID NO: 7) and corresponds to sequences encoding amino acids 1–7. A 30 base 3' oligonucleotide contains an EcoRI site (5'-GAATTCACGTGGGCTTAGCAGTTGCTGTCG-3' SEQ ID NO: 8) and corresponds to a region of cDNA 3' to the endogenous termination codon. A 600 bp fragment is obtained, ligated into pCR II vector, and confirmed by restriction enzyme digest and sequence analysis. The PRL cDNA is cloned into pACT-II via the EcoRI site.

The extracellular domain of the porcine PRL receptor (PRLR) is generated as a fusion to GAL4 DNA binding domain. Oligonucleotides are designed based on sequence of the mouse PRLR (Davis and Linzer, 1989) A 31 base 5' oligonucleotide contains a SmaI site (5'-TCCCCCGGGGATGTCATCTGCACTTGCTTAC-3' SEQ ID NO: 9) while the 31 base 3' oligonucleotide contains a termination codon followed by a SalI site (5' TCCGTCGACGGTCTTTCAAGGTGAAGTCATT-3' SEQ ID NO: 10). These oligonucleotides flank the extracellular domain of the PRLR, encoding amino acids 1–229. A pig pituitary lambda gt11 library is used as template source. Using standard PCR methods, a 687 bp fragment is generated, ligated into pCRII, and the nucleotide sequence is confirmed. The PRLR cDNA is cloned into the pAS2 vector via the SmaI and SalI restriction sites.

Strain Y190 was transformed with the PRL or PRLR fusion expression plasmids either alone (CY727 or CY728, respectively) or together (CY726). Cells expressing both the PRL and PRLR fusions are able to grow on selective medium while the strains containing either the ligand or receptor fusion alone can not. These results mirror those observed in the GH-GHR system in the examples above and establish the general utility of the 2-hybrid system for examination of ligand binding to members of this receptor superfamily.

EXAMPLE 1C

Additional Confirmation of Ligand-Receptor Specificity for the Novel Yeast Host Cell System Additional strains are developed to assess ligand-receptor specificity. URA minus strains expressing GH and GHR fusion proteins are transformed with pCUP or PRL-pCUP; while strains expressing PRL and PRLR fusion proteins are transformed with pCUP, or PRL-pCUP. Briefly, PRL-pCUP is constructed in a fashion similar to that described for GH-pCUP. The PRL cDNA is generated by PCR using a 33 base 5' oligonucleotide with an EcoRI site (5'-GAATTCAAAATGCTGCCCATCTGCCCCAGCGGG-3' SEQ ID NO: 11) and the 3' oligonucleotide in example 1B. The resulting fragment is introduced into pCUP via the EcoRI site. As demonstrated in the above Examples, a strain expressing the GH and GHR fusions with no competitor grows on selective medium and this growth is abolished with coexpression of free GH. The prolactin experiment produces similar results which confirm the specificity of the ligand-receptor binding in the yeast cell. A strain carrying PRL and PRLR fusions (CY787) can grow on selective medium and this growth is abrogated by expression of free PRL (CY786; Table 1).

To test selectivity of the GHR, a strain containing the GH and GHR fusions is transformed with PRL-pCUP. This strain grows on selective medium (CY785; Table 1). These data indicate that GH binding to its receptor in this system can be efficiently competed by excess GH (CY751) binding but not by the related PRL peptide (CY755). The results from the above experiments, expressing three heterologous proteins, illustrates the specificity of ligand-receptor interaction(s) in the system of this invention.

TABLE 1

Strain list and bioassay results

| Designation | AD fusion | BD fusion | pCUP | Growth |
|---|---|---|---|---|
| CY700 | — | — | — | 0 |
| CY722 | GH | GHR | — | + |
| CY723 | vector | GHR | — | 0 |
| CY724 | GH | vector | — | 0 |
| CY726 | PRL | PRLR | — | + |
| CY770 | — | — | — | 0 |
| CY781 | GH | GHR | GH | 0 |
| CY784 | GH | GHR | vector | + |
| CY785 | GH | GHR | PRL | + |
| CY786 | PRL | PRLR | PRL | 0 |
| CY787 | PRL | PRLR | vector | + |

All yeast strains are derived from strain Y190 (Wade Harper et al. 1993). The genotype is MATa gal4 gcl80 his3 trp1-901 ade2-101 ura3-52 leu2-3.112 URA3::GAL-lacZ LYS2::GAL-HIS3 cyh. Strains with number designations equal to or greater than 770 do not have the URA3::GAL-lacZ gene. A dash indicates that a strain does not contain the denoted plasmid.
AD fusions are pACT derivatives; GH or PRL fused to the Ga14 activation domain.
BD fusions are pAS2 derivatives; extracellular domains of GH or PRL receptors fused to the DNA binding domain of Ga14.
pCUP denotes peptides expressed from the pCUP plasmid.
Summary of bioassay results. Each strain is grown on selective medium for 3 to 5 days at 30 C. then scored for cell growth, indicated by a plus.

EXAMPLE 2

Screen for Compounds Disrupting Ligand-Receptor Interaction

Low-copy-number plasmids expressing GHR- or GH-Gal4 fusion proteins (pOZ153 and pOZ152, respectively) are constructed to reduce expression of these proteins. In addition, a novel reporter gene is constructed that prevents cell proliferation on selective medium unless expression is abrogated. To construct the GHR fusion expression plasmid, a SacI-BamHI restriction fragment containing a yeast constitutive promoter and GAL4 sequences is isolated from pAS1 (Durfee et al., 1993) and cloned into pUN30 (Elledge and Davis, 1988). The extracellular domain of GHR is then fused to GAL4 by ligation as an NcoI fragment as described in Example 1 to create pOZ153. To construct the GH fusion expression construct the entire GH-Gal4 region with promoter and terminator sequences is isolated from the plasmid described in Example 1 as a PvuI-SalI fragment. This DNA segment is cloned into pUN100 (Elledge and Davis, 1988) generating pOZ152. A reporter gene is constructed by isolating the yeast CYH2 coding region and operatively linking it to a GAL promoter in a yeast expression plasmid. Briefly, the GAL1 promoter region is inserted into YEp352 (Hill et al., 1986) as a 685 bp EcoRI-BamHI fragment. CYH2 sequences are amplified by PCR using oligonucleotides primers (5'-GGATCCAATCAAGAATGCCTTCCAGAT-3' SEQ ID NO: 12 and 5'-GCATGCGTCATAGAAATAATACAG-3' SEQ ID NO: 13) and pAS2 as the template. The PCR product is digested with BamHI plus SphI and cloned into the corresponding sites in the YEp352-GAL vector. These plasmids are transformed into yeast strain CY770 which carries a mutation at the chromosomal cyh2 gene rendering the strain resistant to the protein synthesis inhibitor cycloheximide. The presence of all three plasmids is necessary to confer cycloheximide sensitivity (cyh5).

The strain (CY857) containing the ligand and receptor fusion plasmids plus the reporter plasmid forms the basis of a simple primary screen for compounds that disrupt the binding of GH to its receptor. Strain CY857 is embedded in standard yeast growth medium containing 10.0 µg/ml cycloheximide. Due to the ligand/receptor interaction driving expression of the CYH2 reporter gene, the strain is cyh- and thus unable to grow. Chemical compounds are placed on this test medium. Compounds which impair GH-GHR binding are identified by the growth of cells surrounding the compounds because in the absence of CYH2 expression the cells become resistant to cycloheximide present in the medium.

Secondary Screen to Determine Target of Sample

Disruption of ligand-receptor binding in this assay can result from reaction of the compound with either the receptor or ligand fusion component. The specific target of the novel compound is determined by a simple secondary assay utilizing strains over-expressing one of the fusion proteins. Strain CY858 expresses the GHR-GAL4 fusion in large excess due to the construct being maintained within the cells at high copy number (pOZ149), while the GH-fusion (pOZ152) is maintained at levels similar to the base strain (CY857). Conversely, strain CY859 expresses the GH-GAL4 fusion in large excess due to this construct being maintained within the cells at high copy number (pKY14), while the GHR fusion (pOZ153) is maintained at levels similar to base strain (CY857). Compounds rescuing growth in the primary screen using CY857 (GH and GHR fusion expressed on low copy numbers plasmids) are then assayed in the same manner using CY858 (GHR>>GH) or CY859 (GH>>GHR) as the test strain. For example, when ligand-receptor binding is inhibited by a compound reacting with the GHR, the secondary screen will demonstrate a detectable change for the phenotype measured. Secondary testing of the rescuing compound on strain CY858 which overexpresses the GHR fusion produces a smaller growth in the presence of the compound than that observed for CY859. This detectable change in the measured phenotype occurs because the overabundance of GHR titrates the compound thereby increasing CYH2 expression and inhibiting cell growth. CY859 produces a detectable change similar to CY857 because the GHR fusion protein is limiting. A compound interacting with the ligand fusion demonstrates the inverse change in measured phenotype in this secondary assay.

EXAMPLE 3

Demonstration of Ligand Dependent Receptor Dimerization

Multiple protein interactions (for example; ligand-receptor-receptor) are investigated with the expanded system which expresses a third protein using the following scheme.

Figure 3:
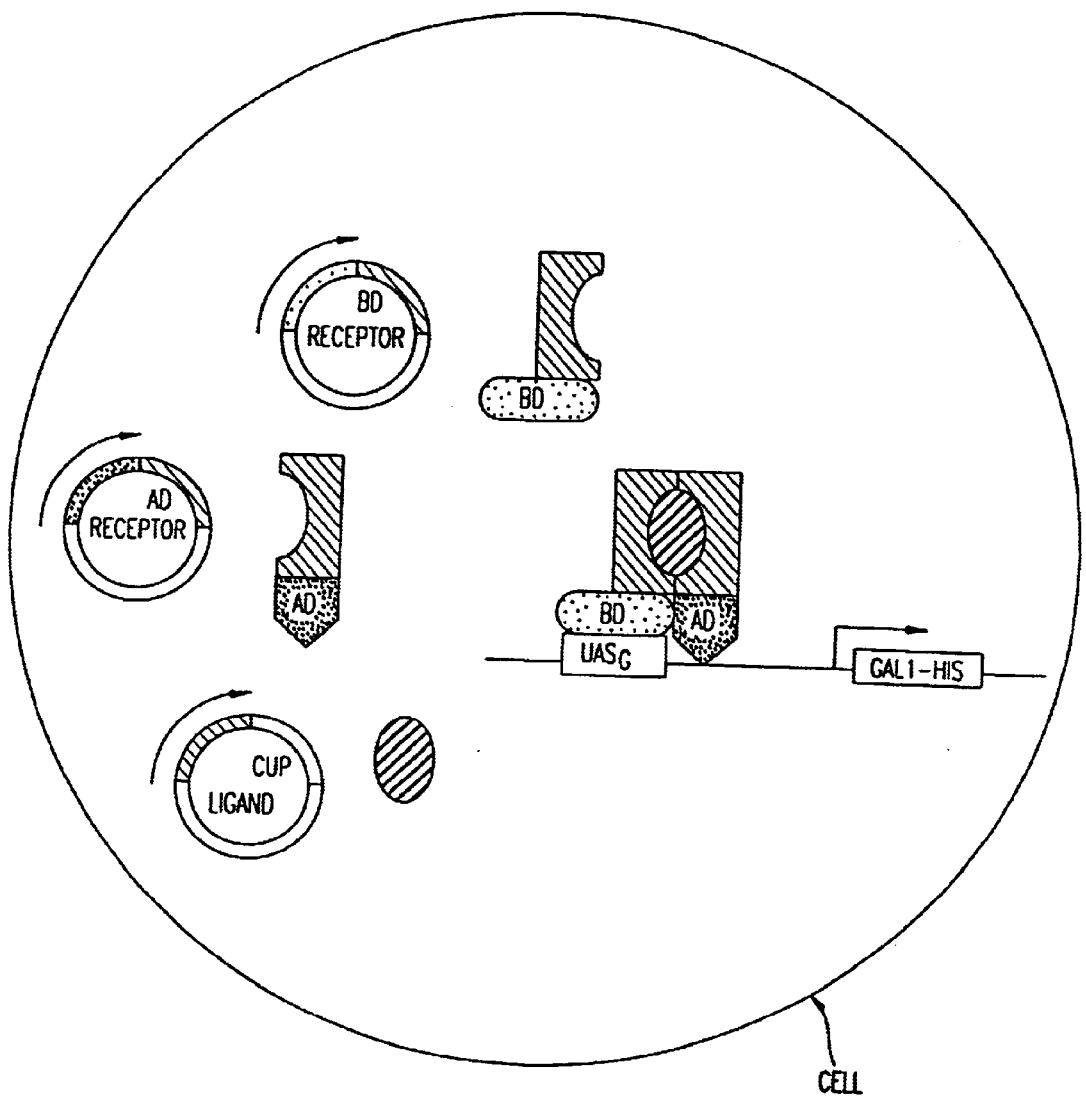
FIG. 3 is a schematic diagram of a dimer model, in which the ligand binds to a dual receptor system. The schematic diagram depicts a cell which expresses proteins from three separate plasmids. Two heterologous fused proteins (one fused protein being a first receptor fused to the activation domain of a transcriptional activation protein and the other fused protein being a second receptor fused to the DNA binding domain of the transcriptional activation protein) are expressed and free ligand (i.e. ligand which is not fused to either of the two domains of the transcriptional activation protein) is expressed from a third plasmid. The figure shows the expression of the two fused proteins and the binding of the free ligand and two receptor fusions which brings together the binding domain and activation domain, reconstituting the transcriptional activation protein. Once the transcriptional activation protein is reconstituted and anchored by the DNA binding domain to the Upstream Activation Sequences (UAS) site, transcription of the receptor gene (HIS3) is initiated.

One unit of the receptor dimer is generated as a fusion protein with either the Gal 4 DNA binding or activation domain. The other unit of the receptor dimer is generated as a fusion protein with corresponding Gal DNA binding or activation domain, whichever is not used for the first fusion. The gene encoding the ligand is expressed from the third plasmid and is produced as a free (non-fusion) ligand. Interaction of the fusion proteins occurs only in the presence of ligand (see FIG. 3).

The interaction of vascular endothelial cell growth factor (VEGF) with the ligand binding domain of its cognate receptor (KDR, kinase insert domain containing receptor) is described as an example for this system. KDR is a tyrosine kinase receptor, and dimer formation (1 ligand-2 receptors) is suggested to be important for hormone-induced receptor function. The cDNA encoding the ligand domain of KDR (Terman et al., 1991) is isolated as an Nco I-BamHI fragment and cloned into both the pACT-II and pAS2 vectors. The cDNA encoding the mature protein for VEGF is generated using standard PCR techniques. Oligonucleotides are designed from published sequence (see Tischer et al., 1991). A 34 base 5' oligonucleotide containing an EcoRI site (5'-CGGAATTCGAAGTATGGCACCCATGGCAGAAGGA-3' SEQ ID NO: 14) and a 28 base 3' oligonucleotide containing an EcoRI site (5'-CGGAATTCGGATCCTCATTCATTCATCA-3' SEQ ID NO: 15) are used to generate a 450 bp fragment encoding the mature protein and cloned into the EcoRI site of pCUP. DNA of final recombinant vectors is transformed into yeast by the lithium acetate method to generate appropriate strains.

Figure 4:
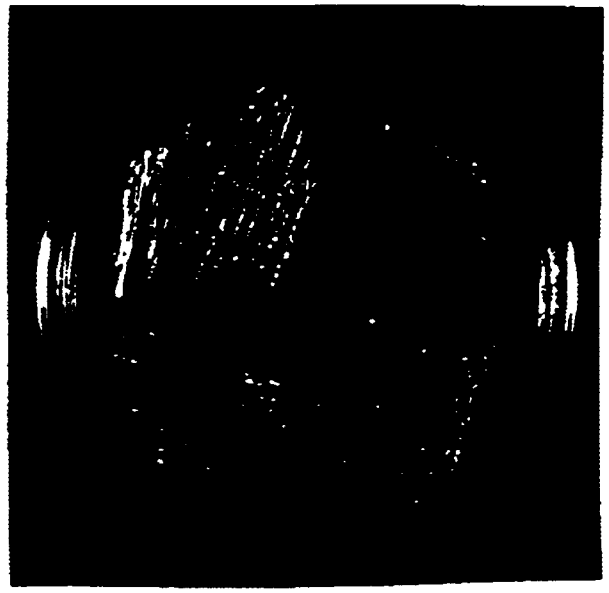
FIG. 4 is a photograph of the growth plate obtained for the strains CY846 and CY847 from Example 3, showing ligand-dependent stimulation of receptor dimerization.

The yeast host strain (CY770) is transformed with KR-pACT-II, KDR-pAS2 and VEGF-pCUP to generate strain CY846; or transformed with both receptor fusions and pCUP to generate strain CY847. Additionally, both KR-pACT-II and KDR-pAS2 are transformed together (CY845) or separately (CY843 or CY844) or VEGF-pCUP alone (CY841) as control strains. Strains are tested for growth on selective medium. The strain (CY846) that expresses the VEGF ligand plus the two receptor fusion proteins exhibits substantial growth on selective media in comparison to the strain CY847, which does not express the VEGF ligand (see FIG. 4). These results demonstrate that the effective cells of this invention can be used to study ligand-dependent dimerization of the receptor.

EXAMPLE 4

Screen for Compounds That act as Ligands in a Dimer Receptor System

Dimerization (oligomerization) of receptor units is often an important first step in activation of receptors such as those for the growth factors, cytokines and those describe supra. The novel cell system described in example 3 can be applied to the discovery of novel compounds which promote (or block) receptor dimerization. Such novel interacting compounds may serve as effective therapeutic agents for pathologies associated with these receptors.

Plasmids expressing the dimer receptor unit(s) as fusion proteins are generated as discussed in example 3. The strain (CY845) containing the KDR-pACT-II and KR-pAS2 fusions serves as an example of a simple primary screen for receptors which exhibit a dimer structure. Strain CY845 is embedded in synthetic agar medium deficient in histidine (Rose et al., 1990). Test compounds are applied to the top of this test medium. Chemical compounds which induce interaction of the two receptor fusions (in the absence of ligand) results in the reconstitution of the endogenous transcriptional activator, which is linked to a reporter gene, such as HIS3. The reconstitution is identified by growth of cells surrounding the compound.

Publications reference above:

Baumback W R, Horner D. and J S Logan. (1989) The growth hormone-binding protein in rate serum is an alternatively spliced form of the rat growth hormone receptor. Genes & Devel. 3: 1199–1205.

Butt T R, Sternberg E J, Gorman J A, Clark P, Hamer D, Rosenberg M and S T Crooke. (1984) Copper metallothionein of yeast, structure of the gene and regulation of expression. Proc. Natn. Acad. Sci. USA 81: 3332–3336.

Chien, C-T., Bartel, P L., Sternglanz R. and S. Fields (1991) The two-hybrid system: A method to identify and clone genes for proteins that interact with a protein of interest. Proc. Natl. Acad. Sci., USA 88: 9573–9582.

Cunningham B C, Ultsch M, De Vos A M, Mulkerrin, M G, Clauser K R and J A Wells. (1991) Dimerization of the extracellular domain of the human growth hormone receptor by a single hormone molecule. Science 254: 821–825.

Davis J and D I H Linzer. (1989) Expression of multiple forms of the prolactin receptor in the mouse liver. Mol. Endocrinol. 3: 674–680.

Davis S, Aldrich T H, Stahl N, Pan L, Taga T, Kishimoto T, Ip N Y and G Yancopoulos. (1993) LIFR and gp 130 as heterodimerizing signal transducers of the tripartate CNTF receptor. Science 260: 1805–1808.

Durfee T., Becherer K., Chen P-L., Yeh, S-H., Yang Y., Wilburn A E., Lee W-H. and S J Elledge. (1993) The retinoblastoma protein associated with the protein phosphatase type 1 catalytic subunit. Genes and Devel. 7: 555–569.

Elledge S J and R W Davis. (1988) A family of versitile centromeric vectors designed for use in the sectering-shuffle mutagenesis assay in Saccharomyces cerevisiae. Gene 70: 303–312.

Fields S and O. Song. (1989) A novel genetic system to detect protein-protein interactions. Nature 340: 245–246.

Finny M. (1992) The polymerase chain reaction. In: Current Protocols in Molecular Biology. Chapter 15 Eds (F M Ausubel, R Brent, R E Kingston, D D Moore, J G Seidman, J Smith and K Struhl) John Wiley & Sons, NY.

Fuh G., Cunningham B C, Fukunaga R, Nagata S, Goeddel D V and J A Wells (1992) Rational design of potent antagonists to the human growth hormone receptor. Science 256: 1677–1680.

Fuh G, Colosi P, Wood W I and J A Wells. (1993) Mechanism—based design of prolactin receptor antagonists. J. Biol. Chem. 8: 5376–5381.

Hill J E, Myers A M, Koerner T J and A Tzagoloff. (1986) Yeast/E. Coli shuttle vectors with multiple unique restriction sites. Yeast 2: 163–167.

Kang Y-S, Kane J, Kurjan J, Stadel J M and D J Tipper. (1990) Effects of expression of mammalian G and hybrid mammalian-yeast G proteins on the yeast pheromone response signal transduction pathway. Mol. Cell. Biol. 10: 2582–2590.

Kondo M, Takeshita T, Ishii N, Nakamura M, Watenabe S, Arai K-i and K Sugamura. (1993) Sharing of the interleukin-2 (IL-2) receptor chain between receptors for IL-2 and IL-4. Science 262: 1874–1877.

Leung D W, Spencer S A, Cachianes G, Hammonds G, Collins C, Henzel W J, Barnard R, Waters M J and W I Wood. (1987) Growth hormone receptor and serum binding protein: purification, cloning and expression. Nature 330: 537–543.

Li, J J and I. Herskowitz (1993) Isolation of ORC6, a component of the yeast origin recognition complex by a one-hybrid system. Science 262: 1870–1874.

Maniatis T, Fritsch E F and J Sambrook. (1982) Molecular Cloning. Cold Spring Harbor Laboratory Press.

Mui A and A Miyajima (1994) Cytokine receptors and signal transduction. In: Progress in Growth Factor Research. pp 15–35. Pergamon Press. NY Noguchi M, Nakamura Y, Russell S M, Ziegler S F, Tsang M, Cao X and W J Leonard. (1993) Interleukin-2 receptor chain: A functional component of the interleukin-7 receptor. Science 262: 1877–1880.

Picard D, Schena M and K R Yamamoto. (1990) An inducible expression vector for both fission and budding yeast. Gene 86: 257–261.

Rose M D, Winston F, and P Hieter. (1990) Methods in yeast genetics. Cold Spring Harbor Laboratory Press.

Staten N R, Byatt J C and G G Krivi. (1993) Ligand-specific dimerization of the extracellular domain of the bovine growth hormone receptor. J. Biol. Chem. 268: 18467–18473.

Su T-Z and M R El-Geweley. (1988) A multisite-directed mutagenesis using T7 DNA polymerase: application for reconstructing a mammalian gene. Gene 69: 81–89.

Taga T and T Kishimoto (1993) Cytokine receptors and signal transduction. FASEB J. 7: 3387–3396.

Taga T, Hibi M, Matsuda T, Hirano T and T. Kishimoto. (1993) IL-6-induced homodimerization of gp130 and associated activation of a tyrosine kinase. Science 260: 1808–1810.

Terman B I, Doucher-Vermanzen M, Carrion M E, Dimitrov D, Armellina D C, Gospodarowicz D and P. Bohlen (1992) Identification of the KDR tyrosine kinase as a receptor for vascular endothelial cell growth factor. Biochem. Biophys. Res. Comm. 187: 1579–1586.

Terman B I, Carrion M E, Kovach E, Rasmussen B A, Eddy R L and Shaws B. (1991). Identification of a new endothelial cell growth factor receptor tyrosine kinase. Oncogene 6: 1677–1683.

Tischer E, Mitchell R, Hartman T, Silva T. Gospodarowicz D, Fiddes J C, and J A Abraham. (1991) The human gene for vascular endothelial growth factor. Multiple protein forms are encoded through alternative exon splicing. J. Biol. Chem. 266: 11947–11954.

Yang, X, Hubbard J A, and M Carlson (1992) A protein kinase substrate identified by the two-hybrid system. Science 257: 31–33.

Young K H and F W Bazer (1989) Porcine endometrial prolactin receptors detected by homologous radioreceptor assay. Mol. and Cell. Endocrinol. 64: 145–154.

Young P R (1992) Protein hormones and their receptors. Curr. Opin. Biotech. 3: 408–421.

Wade Harper J, Adami G R, Wei N, Keyomarsk K and S J Elledge. (1993) The p21 Cdk-interacting protein Cip1 is a potent inhibitor of G1 Cyclin-dependent kinases. Cell 75: 805–816.

Wilson T E, Fahrner T J, Johnston M and J Milbrandt. (1993) Identification of the DNA binding site for NGFI-B by genetic selection in yeast. Science 252: 1296–1300.

What we claim is:

1. A method of detecting the ability of a test sample to affect the binding interaction of a first peptide and a second peptide of a peptide binding pair that bind through extracellular interaction in their natural environment, comprising:

(i) culturing at least one cell, wherein the cell comprises;
   a) a nucleotide sequence encoding a first heterologous fusion protein comprising the first peptide or a segment thereof joined to a transcriptional activation protein DNA binding domain;
   b) a nucleotide sequence encoding a second heterologous fusion protein comprising the second peptide or a segment thereof joined to a transcription activation protein transcriptional activation domain;
   wherein binding of the first peptide or segment thereof and the second peptide or segment thereof reconstitutes a transcriptional activation protein; and
   c) a reporter gene activated under positive transcriptional control of the reconstituted transcriptional activation protein, wherein expression of the reporter gene produces a selected phenotype;
(ii) incubating a test sample with the cell under conditions suitable to detect the selected phenotype; and
(iii) detecting the ability of the test sample to affect the binding interaction of the peptide binding pair by determining whether the test sample affects the expression of the reporter gene which produces the selected phenotype.

2. The method of claim 1 wherein the cell further comprises at least one endogenous nucleotide sequence selected from the group consisting of a nucleotide sequence encoding the transcriptional activation protein DNA binding domain, a nucleotide sequence encoding the transcriptional activation protein transcriptional activation domain, and a nucleotide sequence encoding the reporter gene, wherein at least one of the endogenous nucleotide sequences is inactivated by mutation or deletion.

3. The method of claim 1 wherein the peptide binding pair comprises a ligand and a receptor to which the ligand binds.

4. The method of claim 1 wherein the transcriptional activation protein is Gal4, Gcn4, Hap2, Adr1, Swi5, Ste12, Mcm1, Yap1, Ace1, Ppr1, Arg81, Lac9, Qa1F, VP16, or a mammalian nuclear receptor.

5. The method of claim 1 wherein the reporter gene is selected from the group consisting of lacZ, a gene encoding luciferase, a gene encoding green fluorescent protein, and a gene encoding chloramphenicol acetyltransferase.

6. The method of claim 1 wherein the peptide binding pair is other than an antigen and a corresponding antibody.

7. The method of claim 1 wherein the cell is a eukaryotic, vertebrate, mammalian, amphibian, Xenopus, fungal, Aspergillus, Neurospora, yeast, *Schizosaccharomyces pombe*, or *Pichia pastoris* cell.

8. The method of claim 1 wherein the DNA binding domain is heterologous transcriptional activation protein DNA-binding domain.

9. The method of claim 8 wherein the DNA binding protein is selected from the group consisting of a mammalian steroid receptor and bacterial LexA protein.

10. The method of claim 1 wherein at least one of the heterologous fusion proteins is expressed from an autonomously-replicating plasmid.

11. The method of claim 10 wherein at least one peptide of the peptide binding pair is selected from the group consisting of a cytokine, an interleukin, a hematopoietic growth factor, insulin, an insulin-like growth factor, a growth hormone, prolactin, an interferon, a growth factor, a ligand for G-protein coupled receptors, a ligand for guanylyl cyclase receptors, a ligand for tyrosine phosphatase receptors, and a ligand for tyrosine kinase receptors.

12. The method of claim 11 wherein the peptide is a growth factor selected from the group consisting of epidermal growth factor, nerve growth factor, leukemia inhibitory factor, fibroblast growth factor, platelet-derived growth factor, vascular endothelial growth factor, tumor necrosis factor, oncostatin M, ciliary neurotrophic factor, erythropoietin, steel factor, placental lactogen, and TGF.

13. A rescue screen for detecting the ability of a test sample to affect the binding interaction of a first peptide and a second peptide of a peptide binding pair, comprising:
   (i) culturing at least one cell, wherein the cell comprises;
      a) a nucleotide sequence encoding a first heterologous fusion protein comprising the first peptide or a segment thereof joined to a transcriptional activation protein DNA binding domain;
      b) a nucleotide sequence encoding a second heterologous fusion protein comprising the second peptide or a segment thereof jointed to a transcriptional activation protein transcriptional activation domain;
      wherein binding of the first peptide or segment thereof and the second peptide or segment thereof reconstitutes a transcriptional activation protein; and
      c) a reporter gene activated under positive transcriptional control of the reconstituted transcriptional activation protein, wherein expression of the reporter gene prevents exhibition of a selected phenotype;
   (ii) incubating a test sample with the cell under conditions suitable to detect the selected phenotype; and
   (iii) detecting the ability of the test sample to affect the binding interaction of the peptide binding pair by determining whether the test sample affects the expression of the reporter gene which prevents exhibition of the selected phenotype.

14. The method of claim 13 wherein the cell further comprises at least one endogenous nucleotide sequence selected from the group consisting of a nucleotide sequence encoding the transcriptional activation protein DNA binding domain, a nucleotide sequence encoding the transcriptional activation protein transcriptional activation domain, and a nucleotide sequence encoding the reporter gene, wherein at least one of the endogenous nucleotide sequences is inactivated by mutation or deletion.

15. The method of claim 13 wherein the peptide binding pair comprises a ligand and a receptor for the ligand.

16. The method of claim 13 wherein the transcriptional activation protein is Gal4, Gcn4, Hap1, Adr1, Swi5, Ste12, Mcm1, Yap1, Ace1, Prp1, Arg81, Lac9, Qa1F, VP16, or a mammalian nuclear receptor.

17. The method of claim 13 wherein the receptor gene is selected from the group consisting of a gene that prevents growth on cycloheximide and a gene that prevents growth on canavanine.

18. The method of claim 13 wherein the peptide binding pair is other than an antigen and a corresponding antibody.

19. The method of claim 13 wherein the cell is a eukaryotic, vertebrate, mammalian, amphibian, Xenopus, fungal, Aspergillus, Neurospora, yeast, *Schizosaccharomyces pombe*, or *Pichia pastoris* cell.

20. The method of claim 13 wherein the DNA binding domain is a heterologous transcriptional activation protein DNA-binding domain.

21. The method of claim 20 wherein the DNA binding protein is selected from the group consisting of a mammalian steroid receptor and bacterial LexA protein.

22. The method of claim 13 wherein at least one of the heterologous fusion proteins is expressed from an autonomously-replicating plasmid.

23. The method of claim 22 wherein at least one peptide of the peptide binding pair is selected from the group consisting of a cytokine, an interleukin, a hematopoietic growth factor, insulin, an insulin-like growth factor, a growth hormone, prolactin, an interferon, a growth factor, a ligand for G-protein coupled receptors, a ligand for guanylyl cyclase receptors, a ligand for tyrosine phosphatase receptors, and a ligand for tyrosine kinase receptors.

24. The method of claim 23 wherein the peptide is a growth factor selected from the group consisting of epidermal growth factor, nerve growth factor, leukemia inhibitory factor, fibroblast growth factor, platelet-derived growth factor, vascular endothelial growth factor, tumor necrosis factor, oncostatin M, ciliary neurotrophic factor, erythropoietin, steel factor, placental lactogen, and TGF.

25. A rescue screen for determining whether a test sample interacts with a first or second peptide of a peptide binding pair, comprising:
(i) culturing at least one first cell, wherein the first cell comprises;
  a) a nucleotide sequence encoding a first heterologous fusion protein comprising the first peptide or a segment thereof joined to a transcriptional activation protein DNA binding domain;
  b) a nucleotide sequence encoding a second heterologous fusion protein comprising the second peptide or a segment thereof joined to a transcriptional activation protein transcriptional activation domain;
  wherein the nucleotide sequence encoding the first heterologous fusion protein is present in an effective copy number of at least 5 copies per cell and the nucleotide sequence encoding the second heterologous fusion protein is present at a copy number of 1 or 2 per cell; and
  wherein binding of the first peptide or segment thereof and the second peptide or segment thereof reconstitutes a transcriptional activation protein; and
  c) a reporter gene activated under positive transcriptional control of the reconstituted transcriptional activation protein, wherein expression of the reporter gene prevents exhibition of a selected phenotype;
(ii) culturing at least one second cell, wherein the second cell comprises;
  a) a nucleotide sequence encoding a first heterologous fusion protein comprising the first peptide or a segment thereof joined to a transcriptional activation protein DNA binding domain;
  b) a nucleotide sequence encoding a second heterologous fusion protein comprising the second peptide or a segment thereof joined to a transcriptional activation protein transcriptional activation domain;
  wherein the nucleotide sequence encoding the second heterologous fusion protein is present in an effective copy number of at least 5 copies per cell and the nucleotide sequence encoding the first heterologous fusion protein is present at a copy number of 1 or 2 per cell; and
  wherein binding of the first peptide or segment thereof and the second peptide or segment thereof reconstitutes a transcriptional activation protein; and
  c) a reporter gene activated under positive transcriptional control of the reconstituted transcriptional activation protein, wherein expression of the reporter gene prevents exhibition of a selected phenotype;
(iii) incubating a test sample with the first and second cells under conditions suitable to detect the selected phenotype;
(iv) detecting the presence or absence of the selected phenotype produced by the first and second cells; and
(v) comparing the selected phenotype of the first and second cells, wherein a change in the selected phenotype in one of the cells indicates that the test sample binds to the heterologous fusion protein encoded by the nucleotide sequence present at a copy number of 1 or 2 in that cell exhibiting the change in the selected phenotype, thereby affecting the binding interaction of the peptide binding pair.

26. The method of claim 25 wherein the cell further comprises at least one endogenous nucleotide sequence selected from the group consisting of a nucleotide sequence encoding the transcriptional activation protein DNA binding domain, a nucleotide sequence encoding the transcriptional activation protein transcriptional activation domain, and a nucleotide sequence encoding the reporter gene, wherein at least one of the endogenous nucleotide sequences is inactivated by reconstitution or deletion.

27. The method of claim 25 wherein the peptide binding pair comprises a ligand and a receptor for the ligand.

28. The method of claim 25 wherein the transcriptional activation protein is Gal4, Gcn4, Hap1, Adr1, Swi5, Ste12, Mcm1, Yap1, Ace1, Ppr1, Arg81, Lac9, Qa1F, VP16, or a mammalian nuclear receptor.

29. The method of claim 25 wherein the DNA binding protein is selected from the group consisting of a gene that prevents growth on cycloheximide and a gene that prevents growth on canavanine.

30. The method of claim 25 wherein the peptide binding pair is other than an antigen and a corresponding antibody.

31. The method of claim 25 wherein the first cell and the second cell are the same are a eukaryotic, vertebrate, mammalian, amphibian, Xenopus, fungal, Aspergillus, Neurospora, yeast, *Schizosaccharomyces pombe*, or *Pichia pastoris* cell.

32. The method of claim 25 wherein the DNA binding domain is a heterologous transcriptional activation protein DNA-binding domain.

33. The method of claim 32 wherein the DNA binding protein is selected from the group consisting of a mammalian steroid receptor and bacterial LexA protein.

34. The method of claim 25 wherein at least one of the heterologous fusion proteins is expressed from an autonomously-replicating plasmid.

35. The method of claim 34 wherein at least one peptide of the peptide binding pair is selected from the group consisting of a cytokine, an interleukin, a hematopoietic growth factor, insulin, an insulin-like growth factor, a growth hormone, prolactin, an interferon, a growth factor, a ligand for G-protein coupled receptors, a ligand for guanylyl cyclase receptors, a ligand for tyrosine phosphatase receptors, and a ligand for tyrosine kinase receptors.

36. The method of claim 35 wherein the peptide is a growth factor selected from the group consisting of epidermal growth factor, nerve growth factor, leukemia inhibitory factor, fibroblast growth factor, platelet-derived growth factor, vascular endothelial growth factor, tumor necrosis factor, oncostatin M, ciliary neurotrophic factor, erythropoietin, steel factor, placental lactogen, and TGF.

37. A rescue screen for detecting the ability of a test sample to affect the binding interaction of a first and second peptide of a peptide binding pair, comprising:
(i) culturing at least one cell on a selective medium, wherein the cell comprises;
  a) a nucleotide sequence encoding a first heterologous fusion protein comprising the first peptide or a segment thereof joined to a transcriptional activation protein DNA binding domain;

b) a nucleotide sequence encoding a second heterologous fusion protein comprising the second peptide or a segment thereof joined to a transcriptional activation protein transcriptional activation domain;
wherein binding of the first peptide or segment thereof and the second peptide or segment thereof reconstitutes a transcriptional activation protein;
c) a reporter gene activated under positive transcriptional control of the reconstituted transcriptional activation protein, wherein when the reporter gene is expressed the cell does not grow on the selective medium; and
(ii) incubating a test sample with the cell; and
(iii) detecting the ability of the test sample to affect the binding interaction of the peptide binding pair by determining whether the test sample affects the expression of the reporter gene which prevents growth of the cell on the selective medium.

38. The method of claim 37 wherein the cell further comprises at least one endogenous nucleotide sequence selected from the group consisting of a nucleotide sequence encoding the transcriptional activation protein DNA binding domain, a nucleotide sequence encoding the transcriptional activation protein transcriptional activation domain, and a nucleotide sequence encoding the reporter gene, wherein at least one of the endogenous nucleotide sequences is inactivated by mutation or deletion.

39. The method of claim 37 wherein the peptide binding pair comprises a ligand and a receptor for the ligand.

40. The method of claim 37 wherein the transcriptional activation protein is Gal4, Gcn4, Hap1, Adr1, Swi5, Ste12, Mcm1, Yap1, Ace1, Prp1, Arg81, Lac9, Qa1F, VP16, or a mammalian nuclear receptor.

41. The method of claim 37 wherein the reporter gene is selected from the group consisting of a gene that prevents growth on cycloheximide and a gene that prevents growth on canavanine.

42. The method of claim 37 wherein the peptide binding pair is other than an antigen and a corresponding antibody.

43. The method of claim 37 wherein the first cell and the second cell are the same and are a eukaryotic, vertebrate, mammalian, amphibian, Xenopus, fungal, Aspergillus, Neurospora, yeast, *Schizosaccharomyces pombe*, or *Pichia pastoris* cell.

44. The method of claim 37 wherein the DNA binding domain is a heterologous transcriptional activation protein DNA-binding domain.

45. The method of claim 44 wherein the DNA binding protein is selected from the group consisting of a mammalian steroid receptor and bacterial LexA protein.

46. The method of claim 37 wherein at least one of the heterologous fusion proteins is expressed from an autonomously-replicating plasmid.

47. The method of claim 46 wherein at least one peptide of the peptide binding pair is selected from the group consisting of a cytokine, an interleukin, a hematopoietic growth factor, insulin, an insulin-like growth factor, a growth hormone, prolactin, an interferon, a growth factor, a ligand for G-protein coupled receptors, a ligand for guanylyl cyclase receptors, a ligand for tyrosine phosphatase receptors, and a ligand for tyrosine kinase receptors.

48. The method of claim 47 wherein the peptide is a growth factor selected from the group consisting of epidermal growth factor, nerve growth factor, leukemia inhibitory factor, fibroblast growth factor, platelet-derived growth factor, vascular endothelial growth factor, tumor necrosis factor, oncostatin M, ciliary neurotrophic factor, erythropoietin, steel factor, placental lactogen, and TGF.

49. A rescue screen for determining whether a test sample interacts with a first or second peptide of a peptide binding pair, comprising:
(i) culturing at least one first cell, wherein the first cell comprises;
    a) a nucleotide sequence encoding a first heterologous fusion protein comprising the first peptide or a segment thereof joined to a transcriptional activation protein DNA binding domain;
    b) a nucleotide sequence encoding a second heterologous fusion protein comprising the second peptide or a segment thereof joined to a transcriptional activation protein transcriptional activation domain;
    wherein the nucleotide sequence encoding the first heterologous fusion protein is present in an effective copy number of at least 5 copies per cell and the nucleotide sequence encoding the second heterologous fusion protein is present at a copy number of 1 or 2 per cell; and
    wherein binding of the first peptide or segment thereof and the second peptide or segment thereof reconstitutes a transcriptional activation protein; and
    c) a reporter gene activated under positive transcriptional control of the reconstituted transcriptional activation protein, wherein when the reporter gene is expressed the cell does not grow on the selective medium;
(ii) culturing at least one second cell, wherein the second cell comprises;
    a) a nucleotide sequence encoding a first heterologous fusion protein comprising the first peptide or a segment thereof joined to a transcriptional activation protein DNA binding domain;
    b) a nucleotide sequence encoding a second heterologous fusion protein comprising the second peptide or a segment thereof joined to a transcriptional activation protein transcriptional activation domain;
    wherein the nucleotide sequence encoding the second heterologous fusion protein is present in an effective copy number of at least 5 copies per cell and the nucleotide sequence encoding the first heterologous fusion protein is present at a copy number of 1 or 2 per cell; and
    wherein binding of the first peptide or segment thereof and the second peptide or segment thereof reconstitutes a transcriptional activation protein; and
    c) a reporter gene activated under positive transcriptional control of the reconstituted transcriptional activation protein, wherein when the reporter gene is expressed the cell does not grow on the selective medium;
(iii) incubating a test sample with the first and second cells under conditions suitable to detect the selected phenotype;
(iv) detecting the presence or absence of cell growth by the first and second cells; and
(v) comparing the growth of the first and second cells, wherein growth of one of the cells indicates that the test sample binds to the heterogeneous fusion protein encoded by the nucleotide sequence present at a copy number of 1 or 2 in the growing cell, thereby affecting the binding interaction of the peptide binding pair.

50. The method of claim 49 wherein the cell further comprises at least one endogenous nucleotide sequence selected from the group consisting of a nucleotide sequence encoding the transcriptional activation protein DNA binding domain, a nucleotide sequence encoding the transcriptional activation protein transcriptional activation domain, and a nucleotide sequence encoding the reporter gene, wherein at least one of the endogenous nucleotide sequences is inactivated by mutation or deletion.

51. The method of claim 49 wherein the peptide binding pair comprises a ligand and a receptor for the ligand.

52. The method of claim 49 wherein the transcriptional activation protein is Gal4, Gcn4, Hap1, Adr1, Swi5, Ste12, Mcm1, Yap1, Ace1, Ppr1, Arg81, Lac9, Qa1F, VP16, or a mammalian nuclear receptor.

53. The method of claim 48 wherein the reporter gene is selected from the group consisting of a gene that prevents growth on cycloheximide and a gene that prevents growth on canavanine.

54. The method of claim 49 wherein the peptide binding pair is other than an antigen and a corresponding antibody.

55. The method of claim 49 wherein the first cell and the second cell are the same and are a eukaryotic, vertebrate, mammalian, amphibian, Xenopus, fungal, Aspergillus, Neurospora, yeast, *Schizosaccharomyces pombe*, or *Pichia pastoris* cell.

56. The method of claim 49 wherein the DNA binding domain is a heterologous transcriptional activation protein DNA-binding domain.

57. The method of claim 56 wherein the DNA binding protein is selected from the group consisting of a mammalian steroid receptor and bacterial LexA protein.

58. The method of claim 49 wherein at least one of the heterologous fusion proteins is expressed from an autonomously-replicating plasmid.

59. The method of claim 58 wherein at least one peptide of the peptide biding pair is selected from the group consisting of a cytokine, an interleukin, an hematopoietic growth factor, insulin, an insulin-like growth factor, a growth hormone, prolactin, an interferon, a growth factor, a ligand for G-protein coupled receptors, a ligand for guanylyl cyclase receptors, a ligand for tyrosine phosphatase receptors, and a ligand for tyrosine kinase receptors.

60. The method of claim 59 wherein the peptide is a growth factor selected from the group consisting of epidermal growth factor, nerve growth factor, leukemia inhibitory factor, fibroblast growth factor, platelet-derived growth factor, vascular endothelial growth factor, tumor necrosis factor, oncostatin M, ciliary neurotrophic factor, erythropoietin, steel factor, placental lactogen, and TGF.

* * * * *

UNITED STATES PATENT AND TRADEMARK OFFICE
CERTIFICATE OF CORRECTION

PATENT NO.    : 6,673,540 B1
DATED         : January 6, 2004
INVENTOR(S)   : Kathleen H. Young et al.

It is certified that error appears in the above-identified patent and that said Letters Patent is hereby corrected as shown below:

<u>Column 17,</u>
Line 36, "Hap2," should read -- Hap1, --.

<u>Column 18,</u>
Line 16, "jointed" should read -- joined --.
Line 45, "Prp1," should read -- Ppr1, --.

<u>Column 20,</u>
Lines 24-25, "DNA binding protein" should read -- reporter gene --.
Line 31, "same are" should read -- same and are --.

<u>Column 21,</u>
Line 31, "Prp1," should read -- Ppr1, --.

<u>Column 23,</u>
Line 12, "claim 48" should read -- claim 49 --.

<u>Column 24,</u>
Line 8, "biding" should read -- binding --.

Signed and Sealed this

Thirtieth Day of March, 2004

JON W. DUDAS
*Acting Director of the United States Patent and Trademark Office*